(12) United States Patent
Roux

(10) Patent No.: US 6,373,560 B1
(45) Date of Patent: Apr. 16, 2002

(54) APPARATUS FOR CANDLING EGGS

(75) Inventor: Roland Roux, l'Oie (FR)

(73) Assignee: ECMAS, l'Oie (FR)

( * ) Notice: Subject to any disclaimer, the term of this patent is extended or adjusted under 35 U.S.C. 154(b) by 0 days.

(21) Appl. No.: 09/308,156

(22) PCT Filed: Sep. 4, 1998

(86) PCT No.: PCT/FR98/01902

§ 371 Date: Jun. 16, 1999

§ 102(e) Date: Jun. 16, 1999

(87) PCT Pub. No.: WO99/14589

PCT Pub. Date: Mar. 25, 1999

(30) Foreign Application Priority Data

Sep. 16, 1997 (FR) .............................................. 97 11668

(51) Int. Cl.[7] .......................... A01K 43/00; A01K 43/04
(52) U.S. Cl. .............................. 356/58; 356/53; 356/66; 209/510; 209/511
(58) Field of Search .............................. 356/58, 52, 53, 356/55, 56, 57, 64, 66; 209/510, 511, 509; 250/223 R, 221, 222.1

(56) References Cited

U.S. PATENT DOCUMENTS

| | | | |
|---|---|---|---|
| 3,613,884 A | * 10/1971 | Van Gaalen ................. | 356/53 |
| 4,114,038 A | 9/1978 | Parker ........................ | 250/239 |
| 4,189,849 A | * 2/1980 | van der Schoot .............. | 34/33 |
| 5,745,228 A | * 4/1998 | Hebrank et al. .............. | 356/53 |
| 5,898,488 A | * 4/1999 | Kuhl ........................... | 356/53 |

FOREIGN PATENT DOCUMENTS

| WO | WO 89/06797 | 7/1989 |
|---|---|---|
| WO | WO 96/22528 | 7/1996 |

* cited by examiner

*Primary Examiner*—F. L. Evans
*Assistant Examiner*—Zandra V. Smith
(74) *Attorney, Agent, or Firm*—Young & Thompson

(57) ABSTRACT

An apparatus for candling eggs includes a transmission system of a luminous flux directed towards the egg to be examined and located in its incubation rack a reception device of the luminous flux transmitted after passing through the mass of the egg, and an automatic analyzer of the recorded signals. The transmission system and the reception device are arranged in a vertical plane or a substantially vertical plane, one beneath the eggs to be examined and the other above the latter. A screen protects the transmission system against smears originating from the eggs in the incubation racks.

10 Claims, 1 Drawing Sheet

APPARATUS FOR CANDLING EGGS

BACKGROUND OF THE INVENTION

This present invention relates to an apparatus for candling eggs, i.e. to examine them by transparency, especially in order to select them according to whether they have been fertilised or not.

DESCRIPTION OF THE RELATED ART

Once eggs from chickens, turkeys, pheasants or other poultry have been fertilised, the embryo and the ramifications of blood vessels being formed are rapidly visible by simple transparency. Sorting between fertilised and non-fertilised eggs can be performed visually, but automatic machines fulfilling this function have been developed for quite a long time.

These apparatuses comprise means enabling to determine the absorption factor of a light beam passing through the egg. When this absorption factor reaches a certain threshold, this reflects the presence of an embryo, the sign of fertilisation.

The apparatuses for candling eggs comprise a system transmitting a luminous flux intended to go through the egg, a device receiving the flux transmitted and means of computerised analysis of the signals recorded.

Each egg is analysed individually and the non-fertilised eggs are then put aside manually or automatically.

As a rule, the eggs are analysed directly in their incubation rack arranged horizontally on a conveying device. The transmission system and the reception device are arranged on the same vertical plane, one beneath the said conveying system and the other above the conveying system. The conveying characteristics of the incubation racks are suited to the type of transmitter and receiver used. The structure of these racks enables transparency analysis of the eggs in a vertical plane and the means of analysis used depend on the type or the different types of racks liable to be encountered.

During analysis, it may however happen that smears soil the portion of the device, which is situated beneath the conveying system, for example the transmission system of the luminous flux. These smears may originate from broken eggs, dusts or various waste and they are strongly detrimental to analysis quality.

The aim of the present invention is to overcome the above prior art inconvenience.

To this end, the invention relates to an apparatus for candling eggs of the type composed of a transmission system of a luminous flux directed towards the egg to be examined and located in its incubation rack, and of a device receiving the luminous flux transmitted after passing through the mass of the egg, associated with means of automatic analysis; the transmission system and the reception device are arranged in a vertical plane or a substantially vertical plane, one beneath the eggs to be examined and the other above the latter.

According to the invention, this apparatus comprises a screen protecting the transmission system or the reception device, against smears originating from the eggs or the incubation racks notably, by a gravity effect, which protection screen is made of an appropriate material so as not to disturb the luminous flux and which protection screen is associated with means of automatic cleaning.

According to a preferred embodiment, the transmission system of the luminous flux is placed beneath the eggs to be examined and the detection device above; the smears protection screen is placed between the eggs and the said transmission system.

According to another feature of the invention, the protection screen has the shape of a rotary cylinder in which are located the elements to be protected, and its external face is associated with means of automatic cleaning composed of means intended for the application of a cleaning agent and of a fixed scraping device.

According to another feature, the basis at least of the rotary protection cylinder is immersed in a tub filled with a cleaning agent in order to ensure application of a cleaning film on its external surface, under the action of its own rotation.

Still according to the invention, the protection cylinder is mounted on a fixed axle via lateral flanges, whereas the assembly of the cylinder on the flanges and the assembly of the said flanges on the fixed axle are made watertight. The fixed axle serves advantageously as a support for the elements to be protected, whereas the power supply and the control means of the latter pass through the said axle.

According to another feature, the apparatus comprises means of automatic and continuous conveying of the racks of eggs to be analysed and the protection cylinder is brought into rotation by the driving system of the said conveying means, via a mechanical transmission unit.

Still according to the invention, the apparatus comprises a luminous flux transmission system composed of one or several infrared cells and a camera-type detection system, provided with an infrared filter.

Preferably, a series of transmission systems are adapted to transmit several luminous fluxes, each oriented towards one of the eggs of a given row to be analysed simultaneously and a single detection camera scans the whole corresponding row, to record, then to enable analysing, the luminous fluxes transmitted.

According to another feature, the apparatus comprises a motorised inlet conveyor and a motorised outlet conveyor, between which is placed a supporting tray provided with orifices opposite each egg of the same row, enabling the luminous flux to come through.

BRIEF DESCRIPTION OF THE DRAWINGS

But the invention will be better illustrated, without any limitations, by the following description of a particular embodiment, given solely for exemplification purposes and represented on the appended drawings on which.

DESCRIPTION OF THE PREFERRED EMBODIMENT

Figure 1:
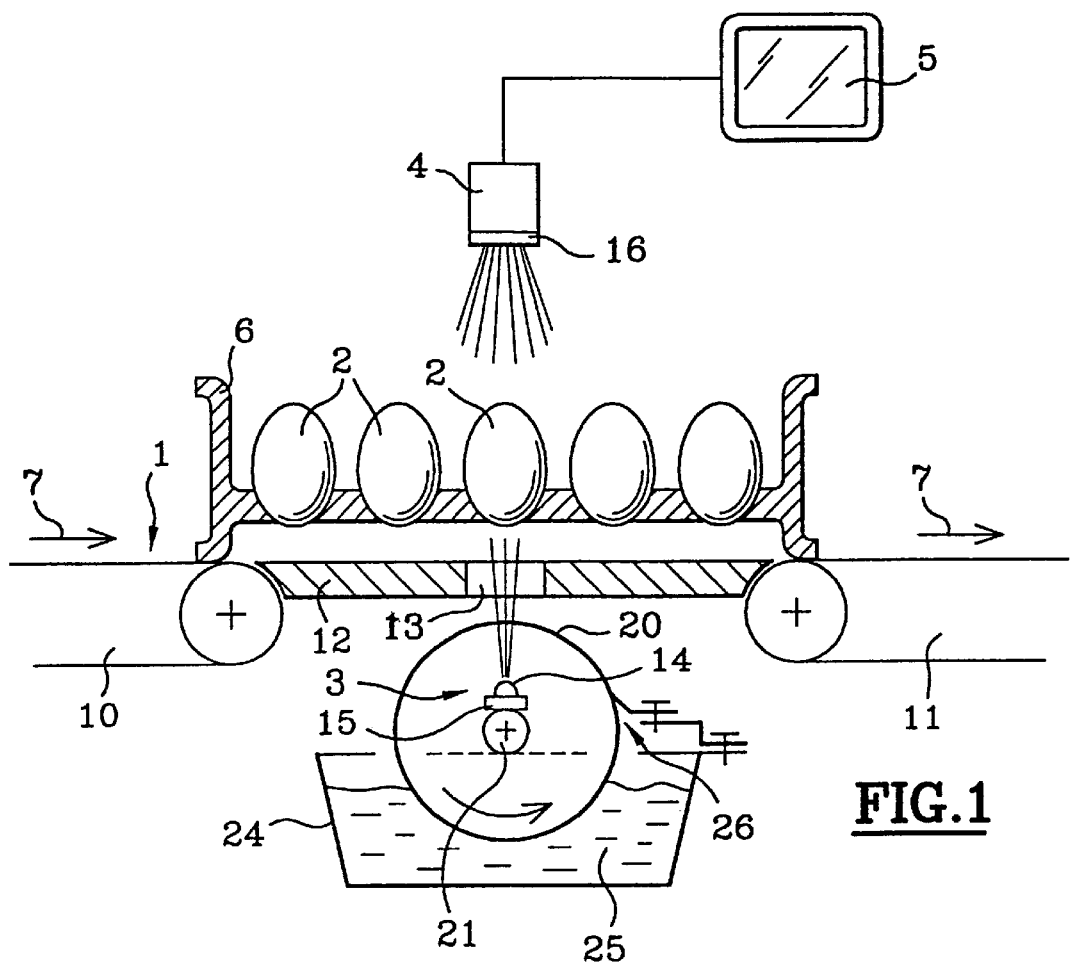
FIG. 1 is a schematic view of an apparatus for candling eggs according to the invention, as a longitudinal cross section.
Figure 2:
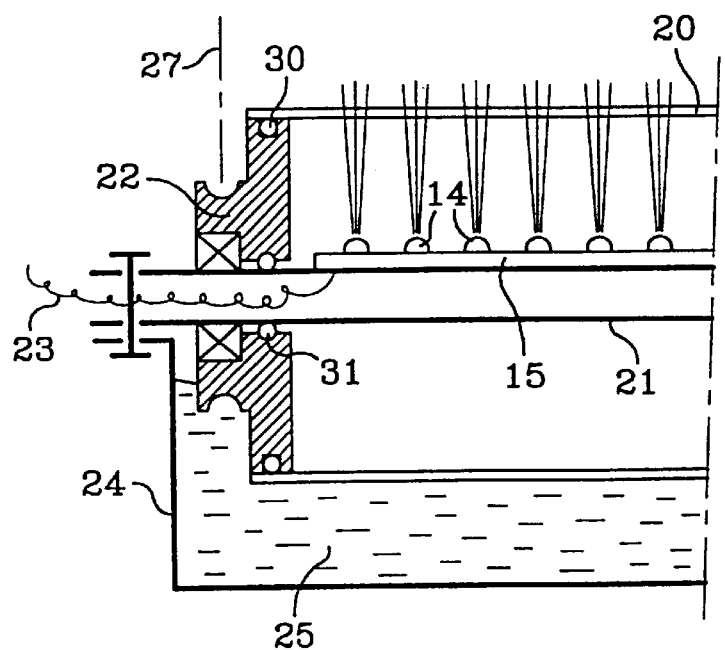
FIG. 2 is an enlarged partial view showing the cylindrical protection tube of the luminous flux transmission system, as an axial cross section.

The candling apparatus represented on FIGS. 1 and 2 is composed of a transport or conveying plane 1 of the eggs 2, beneath which is located the transmission system 3 of an infrared luminous flux and above which is placed the detection device 4, e.g., camera connected to a computerized analyzer 5.

The eggs 2 are arranged in their incubation rack 6 in parallel transversal rows; the racks 6 move in the direction of the orientation arrows 7 and the transmission 3 and detection 4 means are adapted to perform simultaneous analysis of the various eggs in each row.

The transport plane 1 is composed of a motorised inlet conveyor 10 and of a motorised outlet conveyor 11, between which is placed a fixed tray 12 provided with a row of orifices 13 each arranged on the trajectory of a line of eggs.

The tray 12 is situated just beneath the conveying plane; its length is smaller than the length of the incubation racks 6 to ensure their being picked up by the outlet conveyor 11 before they are released from the inlet conveyor 10.

The transmission means 3 of the luminous flux are composed of infrared cells 14 arranged on a horizontal ramp 15 placed transversally to the forward travel direction 7, beneath the tray 12, and more especially beneath the row of orifices 13. One or several infrared cells 14 are provided on the ramp 15 at right angle to each orifice 13 in order to generate the infrared luminous flux towards each egg in the same row in the rack 6. The number of cells 14 per orifice 13 depends on the desirable basic luminous intensity to perform the analysis.

Each infrared luminous flux is oriented towards one of the orifices 13 of the tray 12 in order to reach one of the eggs 2 in the same row in the rack 6. The egg reception cells in the rack 6 comprise an aperture at their bottom so as not to disturb the travel of the light beam.

On the other side of the conveying plane, the luminous intensity of the beam transmitted is detected by the camera 4, which scans the whole width of the same egg row. The lens of the camera is provided with infrared filter 16 capable of taking into account the infrared signals only, in order not to jeopardise the analysis by visible light signals.

The computerized analyzer 5 manages the luminous signal transmitted through each egg to assess whether the egg in question has been fertilised or not. This is a pixel-based image analysis on a determined processing surface.

The racks 6 move continuously and the analysis task takes place during this motion. Images are recorded and analysed very quickly for each egg. In order to perform a timely analysis, the system takes into consideration the pitch between each egg row in the rack 6 as well as a starting signal sent by a system detecting the arrival of the rack.

Beneath the tray 12, the ramp 15 of infrared cells 14 is accommodated in a cylindrical protection tube 20 made of a material such as glass or plastic, capable of not disturbing the passage of the luminous fluxes.

The cylindrical tube 20 is mounted on an axle 21 via lateral flanges 22. The axle 21 extends transversally to the forward travel direction 7; it carries the ramp 15 with the infrared cells 14 and it is preferably hollow to run the power supply and control cables 23 of the said cells.

The cylindrical tube 20 is motorised and rotary mounted on the axle 21, which is fixed. Its base is immersed in a tub 24 containing a cleaning agent 25 (for instance water with a detergent) and a fixed scraper 26 of flexible material, such as rubber, is applied against its external surface. When candling eggs, the protection tube 20 is brought into rotation and its external surface is cleaned permanently by dipping into the cleaning bath 25 and by the action of the scraper 26 that eliminates the residual cleaning film.

The scraper 26 extends over the whole length of the protection tube 20; it is arranged in order to eliminate the cleaning film, possibly together with the smears, upstream of the passage zone of the luminous fluxes, while taking into account the rotation direction of the tube 20.

The cylindrical tube 20 isolates and protects the transmission system 3 against ⌣y external smear originating for instance from a broken egg or from various debris, and its external surface, subjected to constant action of the cleaning agents 25, 26, is kept clean permanently.

The tube 20 can be driven into rotation by a chain, belt or pinion type mechanical transmission unit 27, connected to a direct motorization unit or preferably to the conveyors 10 and 11, or to either of them. One of the lateral flanges 22 of the cylindrical tube 20 is provided accordingly.

As the base of the protection tube 20 is permanently immersed in the cleaning agent 25, a tight assembly should be provided between the tube 20 and its lateral flanges 22 on the one hand, and between the said flanges 22 and the fixed axle 21, on the other hand, thanks to seals, respectively 30 and 31.

The whole portion of the apparatus dedicated to the transmission and the detection of the luminous flux is protected by a casing, not represented, enabling to avoid interference by external light. Beneath the eggs 2 to be analysed, the tray 12 with the orifices 13 enables to limit ingress of possible smears into the transmission system 3, it also enables to channel the infrared light towards the eggs and to limit still further any interference from external light.

The ramp 15 that carries the infrared cells 14 is advantageously mounted in a removable way, with its protection tube 20, or independently, to allow its replacement in case of breakage or failure or even to allow fitting the transmission means 3 to the type of incubation rack used.

With respect to the embodiment illustrated on the figures, it is possible to replace the tub 24 filled with a cleaning agent 25 by nozzles projecting a cleaning agent, without detriment to the cleaning efficiency.

It should also be noted that the same protection principle could be used for the detection device 4 in case when the transmission/reception means 3,4 would be reverted with respect to the embodiment illustrated on the figures.

Moreover, it can be contemplated to adapt this apparatus to provide simultaneous investigation of several egg rows in their incubation rack 6.

What is claimed is:

1. An apparatus for candling eggs, comprising:
   an incubation rack with an orifice;
   a transmission device with an luminous flux source aimed in a direction of the orifice in the incubation rack;
   a detection device positioned in alignment with the luminous flux source to receive luminous flux through the orifice;
   an automatic analyzer connected to the detection device,
   the detection device and the transmission device being arranged in a substantially vertical plane, one beneath the orifice and the other above the orifice;
   a protection screen arranging around and protecting the transmission device or the detection device against smears originating from eggs or the incubation rack,
   the protection screen being made of a material allowing the passage of the luminous flux; and
   an automatic cleaning system position to clean the protection screen.

2. The apparatus of claim 1, wherein,
   the transmission device is located beneath the orifice,
   the detection device is located above the orifice, and
   the protection screen is located between the incubation rack and the transmission device.

3. The apparatus of claim 1, wherein,
   the protection screen is in the shape of a rotary cylinder surrounding either the transmission device or the detection device, and the automatic cleaning system includes a fixed scraping device and elements for applying a cleaning agent to an external face of the protection screen.

4. The apparatus of claim 3, wherein, the protection screen includes a base, and the automatic cleaning system includes a tub filled with a cleaning agent, at least a part of the base being immersed in the cleaning agent.

5. The apparatus of claim 3, wherein the protection screen is mounted on a fixed axle via lateral flanges, the protection screen and flanges forming a watertight assembly.

6. The apparatus of claim 5, wherein, the fixed axle supports either the transmission device or the detection device, and further comprising a power supply and control cable passing through the axle.

7. The apparatus of claim 5, further comprising conveyors located adjacent the transmission device and the detection device, the conveyors being positioned for conveying the incubation rack between the transmission device and the detection device; and a mechanical transmission unit connected to one of the conveyors and to the protection screen, the mechanical transmission unit arranged to rotate the protection screen.

8. The apparatus of claim 1, wherein, the luminous flux source is an infrared cell and the detection device includes a camera with a infrared filter.

9. The apparatus of claim 8, wherein, the transmission device comprises plural luminous flux sources, each of the luminous flux sources oriented toward the incubation rack, and the detection device comprises a single camera arranged to receive and record luminous flux from plural of the luminous flux sources.

10. The apparatus of claim 1, further comprising:

a motorized inlet conveyor and a motorized outlet conveyor; and a tray provided with plural orifices located between the inlet and outlet conveyors, the tray also being located intermediate the transmission device and the detection device.

* * * * *